United States Patent
Tettamanti et al.

(10) Patent No.: US 8,709,057 B2
(45) Date of Patent: Apr. 29, 2014

(54) LASER SYSTEM FOR NON ABLATIVE TREATMENT OF MUCOSA TISSUE

(75) Inventors: Marcelo Tettamanti, Stuart, FL (US); Zdenko Vizintin, Ljubljana (SI); Marko Kazic, Dob (SI); Matjaz Lukac, Ljubljana (SI)

(73) Assignee: Fotona d.d., Ljubljana (SI)

( * ) Notice: Subject to any disclaimer, the term of this patent is extended or adjusted under 35 U.S.C. 154(b) by 0 days.

(21) Appl. No.: 13/348,747

(22) Filed: Jan. 12, 2012

(65) Prior Publication Data

US 2012/0179229 A1 Jul. 12, 2012

(30) Foreign Application Priority Data

Jan. 12, 2011 (EP) .................................... 11000182

(51) Int. Cl.
| | | |
|---|---|---|
| *A61N 5/067* | (2006.01) | |
| *A61B 18/18* | (2006.01) | |
| *A61N 5/06* | (2006.01) | |

(52) U.S. Cl.
CPC .................................. *A61N 5/0603* (2013.01)
USPC ................................................ 607/89; 606/9

(58) Field of Classification Search
CPC ............. A61B 2018/0047; A61B 2017/00765; A61N 2005/0642; A61N 5/0603; A61M 2037/0007
See application file for complete search history.

(56) References Cited

U.S. PATENT DOCUMENTS

| | | |
|---|---|---|
| 5,246,436 A | 9/1993 | Rowe |
| 5,591,157 A | 1/1997 | Hennings et al. |
| 6,156,030 A | 12/2000 | Neev |
| 2004/0010300 A1 | 1/2004 | Masotti |
| 2004/0143248 A1* | 7/2004 | Marchitlo et al. ................ 606/9 |
| 2005/0215987 A1* | 9/2005 | Slatkine ........................... 606/9 |
| 2005/0234527 A1 | 10/2005 | Slatkine |
| 2006/0235492 A1* | 10/2006 | Kemeny et al. ................. 607/88 |
| 2007/0265606 A1 | 11/2007 | DeBenedictis et al. |
| 2007/0276359 A1* | 11/2007 | Segal .............................. 606/11 |
| 2008/0058783 A1* | 3/2008 | Altshuler et al. ................. 606/9 |
| 2008/0188835 A1 | 8/2008 | Hennings |
| 2011/0202116 A1* | 8/2011 | Barolet et al. ................... 607/90 |
| 2012/0078141 A1* | 3/2012 | Knowlton ........................ 601/3 |

FOREIGN PATENT DOCUMENTS

| | | |
|---|---|---|
| WO | 97/35635 A2 | 10/1997 |
| WO | 98/33444 A1 | 8/1998 |
| WO | 2005/081633 A2 | 9/2005 |

\* cited by examiner

*Primary Examiner* — Gary Jackson
*Assistant Examiner* — Scott T Luan
(74) *Attorney, Agent, or Firm* — Gudrun E. Huckett

(57) ABSTRACT

A laser system has a laser source for generating a laser beam, a control unit, and a hand piece for manually guiding the laser beam onto a target area. A wavelength ($\lambda$) of the laser beam is in a range from above 1.9 μm to 11.0 μm inclusive. The laser system is adapted for a thermal, non ablative treatment of mucosa tissue by the laser beam such, that the laser source generates the laser beam in single pulses with a pulse duration ($t_p$) in a range from 1.0 μs, inclusive, to 1.0 sec, inclusive, and that a fluence of each of the single pulses on the target area of the mucosa tissue is in a range from 0.2 J/cm$^2$, inclusive, to 2.5 J/cm$^2$, inclusive, and preferably in a range from 1.40 J/cm$^2$, inclusive, to 1.95 J/cm$^2$, inclusive.

18 Claims, 4 Drawing Sheets

LASER SYSTEM FOR NON ABLATIVE TREATMENT OF MUCOSA TISSUE

BACKGROUND OF THE INVENTION

The invention relates to a laser system for thermal, non ablative treatment of mucosa tissue.

Mucosa is the moist tissue that in addition to some human organs lines body cavities that are exposed to the external environment. They are at several places continuous with skin: at the nostrils, the mouth, the lips, the eyelids, the ears, the genital area, and the anus.

There is a number of health problems that are caused by a deteriorating laxity, elasticity and tightness of mucous membranes and the underlying adjacent tissues (muscles etc.) The following are some of the most common problems: a) involuntary loss of urine called urinary incontinence (UI) among women; b) loss of anal sphincter control leading to the unwanted or untimely release of feces or gas called anal or fecal incontinence; c) vaginal relaxation and the loss of sexual gratification in women and d) snoring.

a) Urinary Incontinence in Women

Millions of women experience involuntary loss of urine called urinary incontinence (UI). Some women may lose a few drops of urine while running or coughing. Others may feel a strong, sudden urge to urinate just before losing a large amount of urine. Many women experience both symptoms. UI can be slightly bothersome or totally debilitating. For some women, the risk of public embarrassment keeps them from enjoying many activities with their family and friends. Urine loss can also occur during sexual activity and cause tremendous emotional distress. Women experience UI twice as often as men. Pregnancy and childbirth, menopause, and the structure of the female urinary tract account for this difference. But both women and men can become incontinent from neurologic injury, birth defects, stroke, multiple sclerosis, and physical problems associated with aging. Older women experience UI more often than younger women. But incontinence is not inevitable with age. UI is a medical problem. Incontinence often occurs because of problems with muscles that help to hold or release urine.

The body stores urine—water and wastes removed by the kidneys—in the bladder, a balloon-like organ. The bladder connects to the urethra, the tube through which urine leaves the body. During urination, muscles in the wall of the bladder contract, forcing urine out of the bladder and into the urethra. At the same time, sphincter muscles surrounding the urethra relax, letting urine pass out of the body.

Worldwide urinary incontinence (UI) is a common problem that affects between 17% to 45% of adult women, often reflected in a deterioration of their social life. The high cost of care for UO, which exceeds 2% of health expenditures in the United States makes this syndrome a public health concern. The most common is Stress Ur. Incontinence (SUI), accounting for 48% of cases, followed by Urge Ur. Incontinence (UUI), caused by an overactive bladder and representing 17% of UI cases. Due to social embarrassment, the taboo or lack of awareness of potential treatments, only a minority of women with UI seek professional help.

One type of incontinence will occur if the sphincter muscles are not strong enough to hold back urine. Treatments involve injections and surgery. A variety of bulking agents, such as collagen and carbon spheres, are available for injection near the urinary sphincter. The doctor injects the bulking agent into tissues around the bladder neck and urethra to make the tissues thicker and close the bladder opening to reduce stress incontinence. A latest surgical technique that uses a polypropylene mesh as prosthetic material reduces the recurrences from 50 to 3%. However, the prosthetic material is autologous and may be rejected. In addition, any surgical procedure (including mesh technique) requires operating theatre, which involves high effort and reduces acceptance by the patient.

b) Fecal Incontinence

Fecal incontinence is one of the most psychologically and socially debilitating conditions in an otherwise healthy individual. Fecal incontinence is a syndrome that involves the unintentional loss of solid or liquid stool. Many definitions of fecal incontinence exist, some of which include flatus (passing gas), while others are confined to stool. True anal incontinence is the loss of anal sphincter control leading to the unwanted or untimely release of feces or gas.

Fecal incontinence has many etiologies. One or a combination of several factors can lead to the inability to control passage of stool or flatus. Vaginal delivery is widely accepted as the most common predisposing factor to fecal incontinence in an otherwise young and healthy woman. Vaginal delivery may result in internal or external anal sphincter disruption, or may cause more subtle damage to the pudendal nerve through overstretching and/or prolonged compression and ischemia.

Many studies support the theory that mechanical sphincter disruption contributes to fecal incontinence. Several surgical procedures are performed for the treatment of anal incontinence. The type of procedure used is based on the patient history, physical examination findings, and results of diagnostic evaluation. The current philosophy in pelvic reconstructive surgery is restoration of normal anatomy. Usually, sphincter complex defects are secondary to obstetric injury, fistula repair, or lateral internal sphincterotomy. The standard procedure for anal incontinence due to anal sphincter disruption is the anterior overlapping sphincteroplasty.

When fecal incontinence persists after medical and surgical therapies have failed, a colostomy may be considered. This converts a perineal stoma into a manageable abdominal stoma and removes the constant fear of public humiliation.

c) Deterioration and Relaxation of Vaginal Tissues

Vaginal relaxation is the loss of the optimum structural architecture of the vagina. This process is generally associated with natural aging and specially affected by childbirth, whether vaginal or not. Multiple pregnancies increase even more the alteration of these structures. During the vaginal relaxation process, the vaginal muscles become relaxed with poor tone, strength, control and support. The internal and external vaginal diameters can greatly increase with a significant stretching of vaginal walls. Under these circumstances the vagina is no longer at its physiologically optimum sexual functioning state. William H. Masters, M.D. and Virginia E. Johnson pioneered studies that concluded that sexual gratification is directly related to the amount of frictional forces generated during intercourse. Friction is a function of the vaginal canal diameter, and when this virtual space is expanded it can lead to reduction, delay or inexistence of orgasms. Thus, vaginal relaxation has a detrimental effect on sexual gratification because of the reduction of frictional forces that diminish sexual pleasure.

Several approaches have been developed to address this issue. The most common current technique utilizes a surgical procedure that requires the cutting and rearrangement of vaginal and peripheral tissue in order to reduce the size of the canal. Operating on or near sensitive vaginal tissue is inherently risky and can cause scarring, nerve damage and decreased sensation. Furthermore, patients require an extended recovery period.

d) Snoring

Snoring is the audible vibration of respiratory structures (inside oral cavity—soft palate and uvula) due to obstructed air movement during breathing while sleeping. In some cases the sound may be soft, but in other cases, it can be rather loud and quite unpleasant. Generally speaking, the structures involved are the uvula and soft palate.

Snoring is known to cause sleep deprivation to snorers and those around them, as well as daytime drowsiness, irritability, lack of focus and decreased libido. It has also been suggested that it can cause significant psychological and social damage to sufferers. Multiple studies reveal a positive correlation between loud snoring and risk of heart attack (about +34% chance) and stroke (about +67% chance).

Surgery is one of the methods that are currently used for correcting social snoring. Some procedures, such as uvulopalatopharyngoplasty, attempt to widen the airway by removing tissues in the back of the throat, including the uvula and pharynx. These surgeries are quite invasive, however, and there are risks of adverse side effects. The most dangerous risk is that enough scar tissue could form within the throat as a result of the incisions to make the airway narrower than it was prior to surgery, diminishing the airspace in the velopharynx.

From US 2007/0265606 A1 an apparatus and method are known, using fractional light based treatment to shrink soft tissue in the mouth of throat to reduce obstruction of the airways for patients suffering from obstructive sleep apnea. A light delivering probe with scanning optics can be used to deliver treatment. Both ablative and non ablative laser light treatments are described. While the ablative laser treatment falls into the above mentioned surgery scenario with all drawbacks, a non ablative treatment has several advantages. When using non ablative lasers, tissue is coagulated to cause shrinkage, but tissue is not removed. The overall impact and burden on the patient's organism is reduced.

However, there are some significant limitations when applying non ablative laser treatment to soft tissue, in particular to mucosa tissue. A laser induced heating has to be provided in the mucosa tissue without overheating to prevent tissue damage and ablation. Heating of the underlying tissue layers has to be minimized. Namely, at high laser powers, the laser tissue interaction can become non-linear leading to ionization and optical breakdown, which may result in an undesirable damage to the tissue. Further, since a minimally invasive, non-ablative, and purely thermal treatment of mucosa is desired the fluence F of the laser must be below or close to the ablation threshold fluence. The fluence is defined as energy density: $F=E/A$ where E is the energy of the laser pulse, and A is the spot size area. Usually it is calculated in $J/cm^2$. The ablation threshold depends on the laser wavelength, and is lower for more strongly absorbed laser wavelengths. Strongly in water absorbed laser wavelengths are above 1.9 μM, as e.g. generated by erbium doted lasers with a wavelength of 2.79 μm or 2.94 μm. This is the reason, why US 2007/0265606 A1 proposes erbium doted lasers for ablation scenarios only, while the wavelength for non ablative treatments is taken as 1.9 μm or below. In summary, laser power, fluence and wavelength are limited, which reduces efficiency of a laser based non ablative mucosa treatment.

The invention has the object to provide means and a method for non ablative treatment of soft tissue, in particular of mucosa tissue, with improved efficiency and minimized impact on the patient's organism.

SUMMARY OF THE INVENTION

This object is solved by a laser system comprising a laser source for generating a laser beam and a control unit and a hand piece for manually guiding the laser beam onto a target area, wherein a wavelength of the laser beam is in a range from above 1.9 μm to 11.0 μm inclusive, and wherein the laser system including the control unit is adapted for a thermal, non ablative treatment of mucosa tissue by means of the laser beam such, that the laser source generates the laser beam in single pulses with a pulse duration in a range from 1.0 μs (microseconds), inclusive, to 1.0 sec (seconds), inclusive, and that a fluence of the laser beam on a target area of the mucosa tissue is in a range from 0.2 $J/cm^2$, inclusive, to 2.5 $J/cm^2$, inclusive, and preferably in a range from 1.4 $J/cm^2$, inclusive, to 1.95 $J/cm^2$, inclusive.

This object is further solved by a method for non ablative treatment of mucosa tissue by using a laser system comprising a laser source for generating a laser beam, a control unit and a hand piece, wherein the laser beam is manually guided onto a target area on the mucosa tissue, wherein a wavelength (λ) of the laser beam is in a range from above 1.9 μm to 11.0 μm inclusive, the method comprising the steps of:

generating with the laser source under control of the control unit the laser beam in single pulses with a pulse duration ($t_p$) in a range from 1.0 μs, inclusive, to 1.0 sec, inclusive;

providing with the laser beam on the target area of the mucosa tissue a fluence of each of said single pulses in a range from 0.2 $J/cm^2$, inclusive, to 2.5 $J/cm^2$, inclusive, and preferably in a range from 1.4 $J/cm^2$, inclusive, to 1.95 $J/cm^2$, inclusive.

An inventive laser system and related inventive method for operation of said laser system are provided for a non-ablative, or minimally ablative, laser thermal tightening and rejuvenation of mucosa and of the adjacent tissues. The device and method are intended for a long-term or temporary elimination or reduction of health problems caused by deteriorating laxity, elasticity and tightness of mucous membranes and the underlying adjacent tissues, based on the following inventive findings:

While the thickness of mucosa varies it is typically several 100 microns thick. For the controlled heat deposition into the mucosa tissue what is needed is an effective and safe heat source that is capable of distributing heat approximately 100 microns deep into mucosa without damaging neither the outside mucous tissue surface nor the deeper lying surrounding tissues.

The proposed inventive laser source as a heat source operates in a wavelength range from above 1.9 to 11 microns, such as Tm:YAG (wavelength of 2.0 microns), Ho:YAG (wavelength of 2.1 microns), Er:YAG (wavelength of 2.94 microns) and Er,Cr:YSGG (wavelength of 2.78 or 2.79 microns), or $CO_2$ (wavelength 10.6 microns) that is highly absorbed in water which is the major content of mucosa. Absorption depths of these laser sources in the human mucosa are in the range from 3 to 300 microns (Er:YAG: 3 microns; Er,Cr:YSGG: 10 microns; CO2: 30 microns and Ho:YAG or Tm:YAG: 300 microns), which ensures that the laser light generated heat is deposited effectively and safely predominately within the mucous tissue.

According to the invention, the laser sources must be pulsed, with pulse widths from 1 microsecond to 1 second. The lower temporal limit ensures that the instantaneous pulse power remains in the linear thermal range of the laser-tissue interactions. Namely, at high laser powers, the laser tissue interaction can become non-linear leading to ionization and optical breakdown, which may result in an undesirable damage to the tissue. And the upper pulse duration limit ensures that the generated heat does not spread via diffusion too far away from the treated volume. Namely, the direct heating by the laser light is followed by thermal diffusion that indirectly heats the deeper lying tissues (indirect heating). For shorter pulses, the time span for thermal diffusion is short, and the heat energy does not reach very deep into the tissue. For longer pulses, the heat has sufficient time to spread deeper into the tissue. The distance to which the heat will diffuse during a laser pulse of a certain pulse width, the pulse duration $t_p$ can be estimated from $x_d=(4D\ t_p)^{1/2}$, where the diffusion constant D for mucosa can be taken to be around $1\times10^{-7}$ m$^2$/s. The upper pulse duration limit of 1 sec thus limits the diffusion depth $x_d$ to below 100 microns, i.e. below the typical thickness of a mucous tissue. The pulse duration of the single pulses is preferably in a range from 10.0 μs, inclusive, to 2,000.0 μs, inclusive, and is in particular at least approximately 600 μs, which showed in practice best results.

Since a non-ablative (or only minimally invasive), and purely thermal treatment of mucosa is desired the fluence of each laser pulse must also be below or close to the ablation threshold fluence. The fluence is defined as energy density: F=E/A where E is the energy of the laser pulse, and A is the spot size area. Usually it is calculated in J/cm$^2$. The ablation threshold depends on the laser wavelength, and is lower for more strongly absorbed laser wavelengths. The ablation threshold depends also on the pulse width=pulse duration, and is lower at longer pulse widths. Appropriate laser parameters will depend on the type of laser system used and the specific treatment indication.

Preferably, erbium doted lasers having a wave length in a range from 2.73 μm, inclusive, to 2.94 μm, inclusive, and in particular an Er:YAG laser with a wave length of 2.94 μm or a Er,Cr:YSGG laser with a wave length in the range from 2.73 μm, inclusive, to 2.79 μm, inclusive are used. Typical preferred Er,Cr:YSGG lasers are cited to have a wavelength of 2.78 μm or 2.79 μm. Such lasers are the most absorbed lasers in mucous tissue, and having the largest range of available pulse widths and fluences. It is thus a preferred source for treating mucosa. For following the above mentioned inventive findings and for meeting the a.m. requirements by using a typical Er:YAG laser, the related pulse widths are from 10 to 2,000 microseconds, and the related fluence of a single pulse is in a range from 0.2 J/cm$^2$, inclusive, to 2.5 J/cm$^2$, inclusive, and preferably in a range from 1.40 J/cm$^2$, inclusive, to 1.95 J/cm$^2$, inclusive, thereby being below or close to the ablation threshold fluence for mucosa.

The proposed laser system and method may be applied to any kind of in particular human mucosa tissue.

With respect to Urinary Incontinence in particular in women, the proposed laser system and method is intended to and capable of reducing the need for surgery or injections by making the tissues thicker and tighter by means of the minimally invasive localized laser heating of the tissues surrounding the urinary sphincter. The advantages of the laser treatment are as follows:

Ambulatory procedure;
No risks of anesthesia, infection and rejection of the material used in traditional techniques;
Very high success rate;
No contraindication;
Does not require antibiotics or painkillers therefore lowers costs, improves the patient's working efficiency and prevent job absenteeism;
The procedure could be easily repeated;
Facilitates the rapid uptake of treatment by patients.

With respect to deterioration and relaxation of vaginal tissues the proposed laser system and procedure delivers a laser beam to generate controlled heat on vaginal structures. A patient experiences an immediate change (tightening) of her vaginal walls, which in turn facilitates the production of higher friction during sexual intercourse, providing enhancement of sexual gratification. This procedure is performed in a short, several minutes treatment sessions and requires no anesthesia. No cuts or wounds are inflicted so all potential undesired collateral effects are minimized.

With respect to snoring, the proposed invention introduces a minimally invasive, non-ablative laser system and method that has the following advantages:

no anesthesia—no needles;
No pre or post-op pain,
Three 15 minutes sessions over 2 months;
Immediate results from the 1st day (more than 50% reduction);
No anesthesia or pre-medication is needed;
Patients can restart their routine life immediately;
No special therapy or care after the laser treatment is needed.

With respect to fecal incontinence the proposed inventive device and process may be analogously applied with related parameters, success and advantages.

Preferably, a pulse sequence with two to fifteen pulses is provided, wherein a sequence duration of the pulse sequence is in a range from 50.0 ms, inclusive, to 1,000.0 ms, inclusive, wherein in particular the pulse sequence comprises four to eight pulses and a sequence duration in a range form 100.0 ms, inclusive, to 500.0 ms, inclusive, and wherein preferably the pulse sequence comprises six pulses and a sequence duration of 250.0 ms. In a preferred embodiment, the cumulative fluence of the pulses of a single pulse sequence on the target area of the mucosa tissue is in a range from 2.0 J/cm$^2$, inclusive, to 20.0 J/cm$^2$, inclusive, preferably in a range from 5.0 J/cm$^2$, inclusive, to 15.0 J/cm$^2$, inclusive, and is in particular in a range from 8.0 J/cm$^2$, inclusive, to 12.0 J/cm$^2$, inclusive. Expediently, multiple pulse sequences follow each other with a sequence repetition time in a range from 0.5 s, inclusive, to 2.0 s, inclusive, and preferably at least approximately of 0.625 s.

When higher doses of heat are required to be delivered to the mucous tissue without over-reaching the ablation threshold, a special "smooth" pulse mode technique is proposed in our invention, by applying the a.m. pulse sequence or pulse sequences. In said "smooth" pulse sequence mode the energy is delivered to mucosa in a consecutive sequence of several individual laser pulses where the fluence of each of the individual laser pulses in the sequence is below or close to the ablation threshold, i.e. from 0.2 J/cm$^2$, inclusive, to 2.5 J/cm$^2$, inclusive, and preferably in a range from 1.40 J/cm$^2$, inclusive, to 1.95 J/cm$^2$, inclusive. When the temporal separation among the pulses is longer than the thermal relaxation time (TRT) of the mucous surface tissue, the surface mucous tissue has sufficient time to cool between the pulses by dissipating the heat into the deeper tissue layers. Thus temperatures required for ablation are reached at much higher fluences. The TRT is the time required for the tissue temperature to decrease by approximately 63%. And if at the same time laser energy is delivered in a time period that is shorter than the TRT of the total mucous layer (estimated to be in the range of 0.5-1 sec) then the deeper lying mucous layer does not have time to cool off during the laser pulse sequence. The delivered laser energy thus results in an overall non ablative build-up of heat and creates a temperature increase deep in the mucous and sub-mucous tissue. The above principle is employed when the super-long pulses of Smooth mode are used. Because the super-long Smooth pulses are longer than the mucous surface TRT, the total or cumulative allowable fluence is much higher than that of a single laser pulse (1-2 J/cm$^2$ in the case of Er:YAG), without reaching the conditions for ablation.

In an preferred embodiment, as an alternative to the "smooth pulses" being the a.m. pulse sequences, single pulses in a continuous sequence may be provided, having a pulse frequency in a range from 5.0 Hz, inclusive, to 30.0 Hz, inclusive, and preferably of at least approximately 10.0 Hz.

In a preferred embodiment, the laser system is configured and used to irradiate with resting hand piece an irradiation area on the target area, said irradiation area having a mean area diameter in a range from 0.3 mm, inclusive, to 20.0 mm, inclusive, in particular from 5.0 mm, inclusive, to 10.0 mm, inclusive, and preferably of at least approximately 7.0 mm.

Expediently, an irradiation area generated with resting hand piece is irradiated by the laser beam in single target dots having a mean dot diameter in a range from 0.3 mm, inclusive, to 3.0 mm, inclusive, and preferably of at least approximately 0.4 mm. Preferably, means for generating the target dots are provided, in particular in form of a scanner, a screen, a lens array or a diffractional lens.

In order to reduce pain, and facilitate faster healing following the treatment our invention also includes a non-uniform, patterned irradiation of the tissue. The reason to have healthy untouched spots around the heated tissue is to use the capacity of healthy spot tissue and cells for fast immune response and would healing process. Our clinical experience also shows that patterned irradiation is more comfortable to the patient, which allows practitioners to use higher fluences within the irradiated spots. The patterned irradiation can be accomplished by installing a mechanical screen or another suitable optical element into a handpiece, or by patterning the irradiation using a scanner.

In a preferred embodiment, the handpiece has an exit side, wherein an adapter piece is disposed on the exit side, wherein a guide element is provided for immediate contact with the target area and as an receptacle and guide for the adapter piece, and wherein the adapter piece is longitudinally and/or rotationally movable within the guide element. Expediently, the guide element comprises radial distance means for the adapter piece relative to the target area, wherein the radial distance means are in particular comprised of struts, being disposed axially parallel to the guide element and distributed around the adapter piece.

Said arrangement is suitable for treating mucosa in any body opening, and in particular to treat vaginal mucosa. In a related process, when the mucosa on the inner vaginal walls is treated to provide a laser assisted stress urinary incontinence treatment or a laser vaginal tightening treatment, the unit comprising the guide element and the handpiece including its adapter piece is inserted into the vagina. The guide element is kept there in place, and then not moved much or not moved at all, thereby keeping the mucosa tissue in a desired distance to the handpiece. The inner part, i.e. the handpiece and its adapter piece with an optional mirror at the end, can be rotated and moved longitudinally in order to treat the whole inner surface of the vagina, thereby providing a reference system for the handpiece movement, which allows a well defined movement a homogeneous surface treatment. The handpiece including its adapter piece may be manually moved relative to the guide element, but a motor driven movement may be advantageous as well.

Preferably, when the guide element comprises longitudinal struts, and when within at least one application session the laser beam is guided over the target area in multiple passes, then between two sequential passes the guide element is turned about its longitudinal axis. This prevents the target area of being shielded against the laser beam by the longitudinal struts at the same location.

In a preferred embodiment, when providing a laser assisted stress urinary incontinence treatment or a laser vaginal tightening treatment, an adapter piece having an angular flat mirror is used, wherein the target area is defined by the anterior vaginal wall, and wherein the adapter piece is at least longitudinally moved within the guide element, thereby guiding the laser beam over the target area. By using the angular flat mirror the beam can be directed onto the anterior vaginal wall precisely at the desired locations, without influencing the surrounding tissue.

It has been found effective for the a.m. process, that within one application session the adapter piece is longitudinally moved relative to the guide element in at least one, preferably in three to seven, and in particular in five passes, wherein the longitudinal movement is performed in fifteen to twenty-five, in particular in nineteen steps, and wherein between each individual pass the adapter piece with the angular flat mirror is turned such, that the laser beam is guided onto a sub-area of the target area adjacent to and overlapping with a sub-area already being irradiated during a preceding pass. In each single step, the hand piece is resting, thereby providing a desired number of pulses or "smooth pulses" in a stacked manner on the very same location.

In a preferred alternative embodiment, when providing a laser assisted stress urinary incontinence treatment or a laser vaginal tightening treatment, an adapter piece having a conical mirror is used, wherein the target area is defined by the 360° circumferential vaginal wall, and wherein the adapter piece is at least longitudinally moved within the guide element, thereby guiding the laser beam over the target area. The conical mirror generates a quasi cylindrical irradiation pattern, thereby irradiating the circumferential vaginal wall in 360° without the need to turn the hand piece or adapter piece. However, between two sequential passes the guide element may be turned about its longitudinal axis to prevent shielding by the struts.

It has been found effective for the a.m. process, that within one application session the adapter piece is longitudinally moved relative to the guide element in at least one, preferably in two to six, and in particular in four passes, wherein the longitudinal movement is performed in fifteen to twenty-five, in particular in twenty steps. Again, in each single step, the hand piece is resting, thereby providing a desired number of pulses or "smooth pulses" in a stacked manner on the very same location.

BRIEF DESCRIPTION OF THE DRAWINGS

Embodiments of the invention will be explained in the following with the aid of the drawing in more detail.

DESCRIPTION OF PREFERRED EMBODIMENTS

Figure 1:
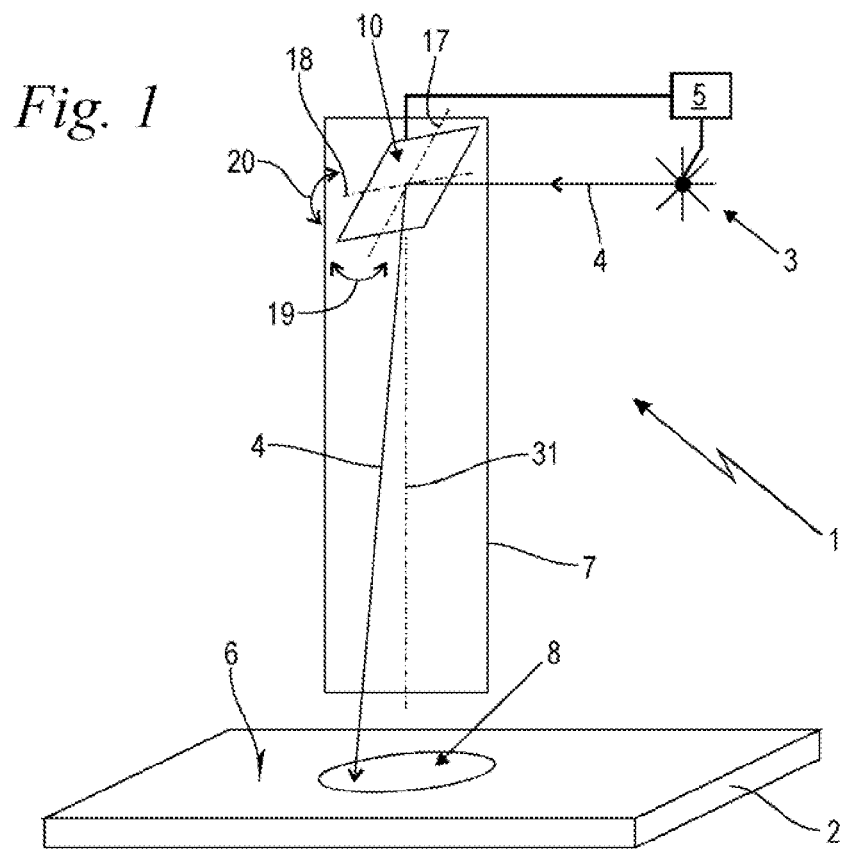
FIG. 1 is a schematic view of an inventive laser system with a handpiece, a scanner and a control unit for treating mucosa.

FIG. 1 shows in a schematic view a first embodiment of the inventive laser system 1. The laser system 1 comprises a laser source 3 for generating a laser beam 4, a hand piece 7 for manually guiding the laser beam 4 to a target area 6, and a control unit 5, which controls the operation of the laser source 3 for generating the laser beam 4 in an inventive mode as described infra. The hand piece 7 optionally contains a scanner 10 with a mirror, which is rotationally movable about two axes 17, 18, as indicated by corresponding arrows 19, 20. The axes 17, 18 are perpendicular to each other. In a neutral position without any mirror deflection, the incoming laser beam 4 is deflected by 90°. However, any other neutral deflection angle may be chosen as well. In the neutral position of the scanner mirror, the deflected laser beam 4 passes the hand piece 7 along its longitudinal axis 31, until it impinges on an irradiation area 8 as part of the target area 6. Upon controlled movement of the scanner mirror, the laser beam 4 is deflected to any desired angle relative to the longitudinal axis 33. The scanner 10 and its mirror movement is controlled by the control unit 5 in such a manner, that, with the hand piece 7 resting in a certain position without any movement relative to the target area 6, and the irradiation area 8 on the target area 6 is irradiated in any desired shape and intensity distribution, as controlled by the correspondingly adapted control unit 5.

The inventive laser system 1, in particular its laser source 3 and its control unit 5, is adapted for thermal, non-ablative treatment of mucosa tissue 2 by means of the laser beam 4, as described in more detail infra. Human mucosa tissue 2 and a target area 6 thereon are schematically shown, with the target area 6 and the irradiation area 8 facing the exit side of the hand piece 4. The hand piece 4 is manually guided relative to the mucosa tissue 2 such, that the irradiation area 8 is irradiated by the laser beam 4. Upon movement of the hand piece 2 relative to the mucosa tissue 2, the irradiation area 8 is moved correspondingly, as a consequence of which the entire target area 6 may be irradiated and thereby treated in any desired pattern.

Figure 2:
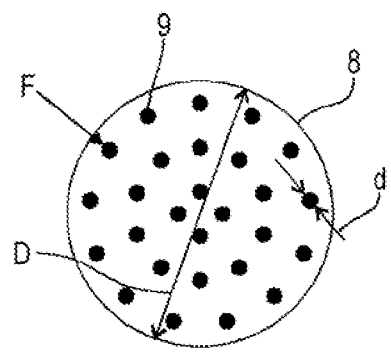
FIG. 2 is a schematic view of the treated mucosa irradiation area with a dotted irradiation pattern as generated by the laser system according to FIG. 1.

FIG. 2 shows a schematic top view of the treated mucosa irradiation area 8 of FIG. 1, having in the shown embodiment a circular shape. However, any other desired shape as an elliptical, polygonal or rectangular shape may be chosen as well. In particular, a quasi cylindrical irradiation area 8 may be generated, when using an adapter piece 13 having a conical mirror 28, as described along with FIG. 7. The irradiation area 8 of FIG. 2 has a mean area diameter D, being preferably in a range from 0.3 mm, inclusive, to 20 mm, inclusive, and in particular from 5.0 mm, inclusive, to 10.0 mm, inclusive. In the shown preferred embodiment, the mean area diameter D is at least approximately 7.0 mm.

The irradiation area 8 may be homogeneously irradiated by an appropriate movement pattern of the scanner 10 (FIG. 1), thereby causing a single irradiation dot in the shape and size of the irradiation area 8. In this specific case, the scanner 10 (FIG. 1) may be omitted, while an accordingly designed, not shown optical arrangement images the laser beam 4 (FIG. 1) onto the irradiation area 8 in the desired shape and size. In the shown preferred embodiment, the irradiation area 8 is irradiated by the laser beam 4 (FIG. 1) in a specific pattern, consisting of multiple target dots 9. According to the embodiment of FIG. 1, the means for generating the target dots 9 are provided in form of the scanner 10. However, different means for generating said target dots 9 may be chosen, such as a screen 11 as described along with FIG. 5, a lens array or a diffractional lens. In the shown embodiment, a total of twenty seven target dots 9 within the irradiation area 8 are chosen. However, different numbers of target dots 9 may be desirable as well. The target dots 9 preferably have a mean dot diameter d in a range from 0.3 mm, inclusive, to 3.0 mm, inclusive. In the shown embodiment, the mean dot diameter d is at least approximately 0.4 mm. The target dots 9 are irradiated by the laser beam 4 (FIG. 1) with a fluence F.

Referring back to FIG. 1, the laser system 1 including its laser source 3 is adapted to generate the laser beam 4 with a wave length λ in a range from above 1.9 µm to 11.0 µm, inclusive. Any suitable laser source 3 for generating said wave length λ may be chosen. Preferably, the laser source 3 is an erbium doted laser having a wave length λ in a range from 2.73 µm, inclusive, to 2.94 µm, inclusive, and may be an Er,Cr:YSGG laser with a wave length λ in the range from 2.73 µm, inclusive, to 2.79 µm, inclusive, preferably of 2.78 µm or 2.79 µm. In the shown preferred embodiment, the laser source 3 is an Er:YAG laser with a wave length λ of 2.94 µm.

Figure 3:
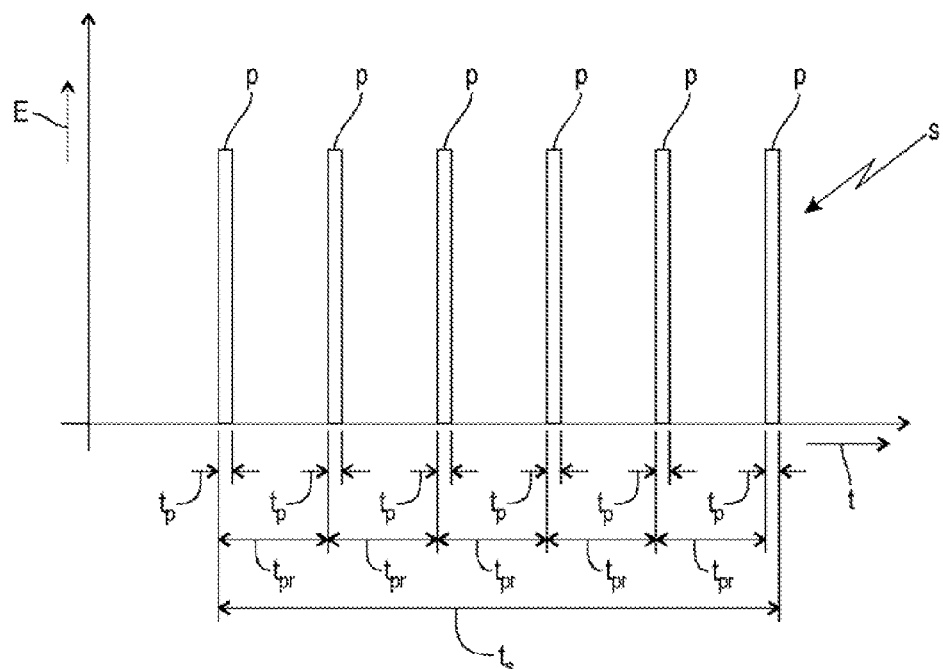
FIG. 3 shows a diagram showing an inventive pulse sequence with individual pulses as generated by the laser system according to FIG. 1.

The laser source 3 is controlled by the control unit 5 in such a manner, that the laser source 3 generates the laser beam 4 in single pulses p, as shown in the diagram of FIG. 3. In the diagram of FIG. 3, the emitted laser energy E and its distribution over the time t is shown, wherein the energy E is typically measured in Joule. Single pulses p in a consecutive sequence of any desired sequence length may be generated. In one preferred embodiment of FIG. 3, single pulses p in a continuous sequence are provided, having a pulse frequency in a range from 5.0 Hz, inclusive, to 30.0 Hz, inclusive, and preferably of at least approximately 10.0 Hz, corresponding to a pulse repetition time $t_{pr}$ in a range from 200 ms, inclusive, to 33.33 ms, inclusive, and preferably of at least approximately 100 ms. In connection with the afore mentioned continuous pulse sequence, within at least one application session the laser beam 4 is preferably guided over the target area 6 in multiple passes, wherein in a first and in a second application session seven to eight passes are provided, and wherein in a third, final session four passes are provided. In one preferred alternative embodiment according to FIG. 3, a number of pulses p are summarised in a pulse sequence s, preferably with two to fifteen pulses, wherein a sequence duration $t_s$ of the pulse sequence s is in a range from 50.0 ms, inclusive, to 1,000.0 ms, inclusive. In particular, the pulse sequence s comprises four to eight pulses p and a sequence duration $t_s$ in a range from 100.0 ms, inclusive to 500.0 ms, inclusive. In the shown preferred embodiment the pulse sequence s comprises six pulses p and an overall total sequence duration $t_s$ of at least approximately 250.0 ms. Each one of such pulse sequences s forms a so called "smooth pulse".

Every single pulse p has a pulse duration $t_p$ in a range from 1.0 µs, inclusive, to 1.0 sec, inclusive, and preferably in a range from 10.0 µs, inclusive, to 2,000.0 µs, inclusive. In the shown preferred embodiment, the pulse duration $t_p$ is at least approximately 600 µs. The individual single pulses p follow each other in a pulse repetition time $t_{pr}$ of at least approximately 50.0 ms, which leads together with said six pulse p to said total sequence duration $t_s$ of approximately 250.0 ms.

Under simultaneous reference to FIGS. 1, 2 and 3, the energy E of each single pulse p is chosen to obtain a certain fluence F on the irradiation area 8 (FIG. 2), wherein the fluence F=E/A, with E being the energy E of FIG. 3, and with A being the irradiated area. The irradiated area A is derived from the target dots 9 and their mean dot diameter d. In the case, that not a fractional, dotted irradiation pattern according to FIG. 2 is chosen, but a full-field beam is applied to the irradiation area 8, the area A is derived from the irradiation area mean diameter D. the energy E of every single pulse p, the number of target dots 9 and their mean dot diameter d are adapted in such a manner, that with every single pulse p a fluence F is generated in the irradiation area 8, respectively in its target dots 9, being in a range from 0.2 J/cm$^2$, inclusive, to 2.5 J/cm$^2$, inclusive, and preferably in a range from 1.40 J/cm$^2$, inclusive, to 1.95 J/cm$^2$, inclusive, thereby being below but close to ablation threshold fluence of the mucosa tissue 2. Within one single pulse sequence s consisting of multiple pulses p the cumulative fluence F generated by the pulses p, i.e. the fluence sum of all pulses p within one single pulse sequence s is according to the invention in a range from 2.0 J/cm$^2$, inclusive, to 20.0 J/cm$^2$, inclusive, preferably in a range from 5.0 J/cm$^2$, inclusive, to 15.0 J/cm$^2$, inclusive, and in particular in a range from 8.0 J/cm$^2$, inclusive, to 12.0 J/cm$^2$, inclusive. In the shown embodiment the cumulative fluence F is at least approximately 9.6 J/cm$^2$.

Figure 4:
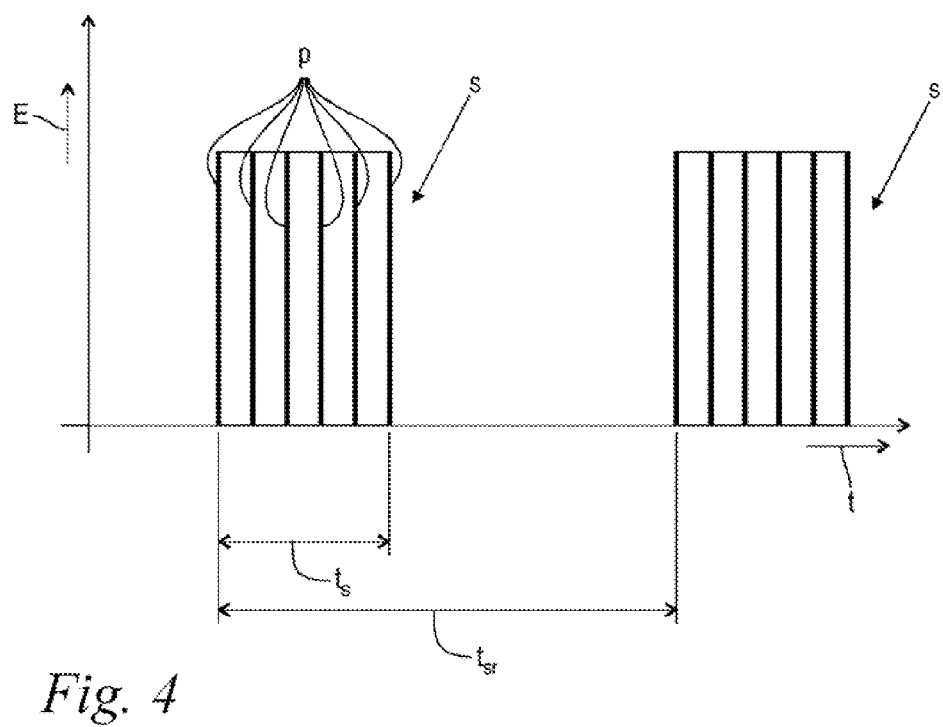
FIG. 4 shows a diagram showing an inventive train of multiple pulse sequences according to FIG. 3.

FIG. 4 shows a diagram of an inventive train of multiple pulse sequences s according to FIG. 3. Multiple pulse sequences s, each consisting of pulses p according to FIG. 3, follow each other in sequence repetition times $t_{sr}$. According to the invention, the sequence repetition time $t_{sr}$ is in a range from 0.5 sec, inclusive, to 2.0 sec, inclusive, preferably in a range from 0.5 s, inclusive, to 1.0 s, inclusive, and is in the shown preferred embodiment at least approximately 0.625 sec, corresponding to a sequence repetition rate of 1.6 Hz. The hand piece 7 is preferably guided along the target area 6 in a stepped movement such, that within one single step with resting hand piece 7 two to six and in particular four subsequent pulse sequences s are guided on the same location, i.e. on the same unmoved irradiation area 8 within the target area 6.

Within the aforementioned limitations, every single pulse sequence s consisting of individual pulses p forms a single "smooth pulse", which follow each other in the sequence repetition time $t_{sr}$, thereby introducing high amounts of energy E into the mucosa tissue 2 (FIG. 1) without ablation or damage of the mucosa tissue 2 for a non-ablative, pure thermal treatment.

Figure 5:
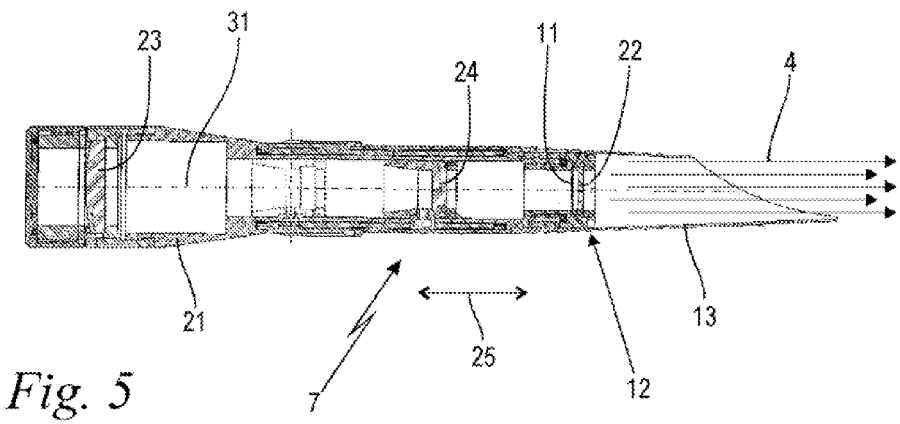
FIG. 5 shows a variant of the handpiece according to FIG. 1 with straight beam delivery and a screen to produce a dotted irradiation according to FIG. 2.

FIG. 5 shows in a sectional view a further embodiment of the hand piece 7, comprising a main body 21 with an exit side 12, to which an adapter piece 13 is attached. The adapter piece 13 is a straight tube, being coaxially disposed to the longitudinal axis 31 of the hand piece 7, and allowing the laser beam 4 to exit the hand piece 7 coaxially to the longitudinal axis 31, thereby generating an irradiation pattern on the irradiation area 8 according to FIG. 2. Close to the exit side 12 a protective window 22 is arranged, which protects the interior of the hand piece 7, but which allows the laser beam 4 to pass unhindered. At the inner side of the protective window 22 a screen 11 is disposed, which acts as means for generating the target dots 7 (FIG. 2) as an alternative to the scanner 10 (FIG. 1). The screen 11 may be disposed at different suitable locations as well. In particular it may be disposed outside the protective window 22 or even replace the protective window 22.

The hand piece 7 contains a number of lenses 23, 24 in order to collimate the laser beam 4 after passing the screen 11 on the individual target dots 9 (FIG. 2). For doing so, the lens 24 may be coaxially moved relative to the lens 23 as indicated by an arrow 25, until the desired collimation has been achieved.

The handpiece 7 including its straight adapter piece 13 is preferably utilized for non-ablative treatment of mucosa to provide a laser assisted snoring reduction or a laser assisted stress urinary incontinence treatment, where free access to the mucosa tissue is given. The practitioner may manually guide the hand piece 7 an in consequence the laser beam 4 to the target area 6. In laser assisted snoring reduction, the target area 6 is the anterior mouth or throat pillar extending to the outer face up to the retromolar region and posterior third of the cheek, the soft palate and uvula with lower part of the hard palate, posterior pillars and tonsils, lateral and bottom of the tongue. In laser assisted stress urinary incontinence treatment, the target area 6 is the vestibule and urethral sphincter area.

Figure 6:
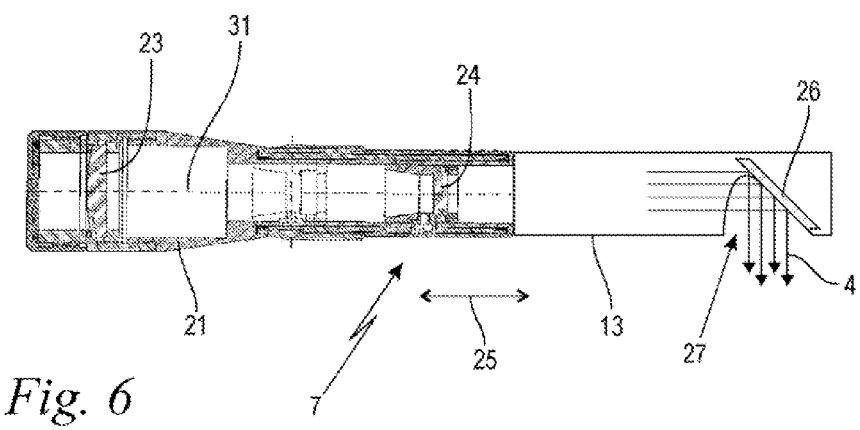
FIG. 6 shows a variant of the handpiece according to FIG. 5 with a flat mirror for angular beam delivery.

FIG. 6 shows a variant of the hand piece according to FIG. 5 with a different arrangement of the adapter piece 13. The schematically shown adapter piece 13 holds a flat mirror 26 in an angle of 45° relative to the longitudinal axis 31 and provides an opening 27 in the surrounding wall of the adapter piece 13, which allows the laser beam 4 to exit the adapter piece 13 in a radial direction after being deflected from the flat mirror 26. The 45° angle of the flat mirror 26 results in a 90° deflection of the laser beam 4. However, any other suitable angle of the flat mirror 26 may be chosen as desired. In any case, the radially deflected laser beam 4 results in the same irradiation pattern as generated by the hand piece 7 of FIG. 5 with the only difference, that the irradiation area 8 (FIG. 2) is not located around the longitudinal axis 31, but in the radial position thereto.

Figure 7:
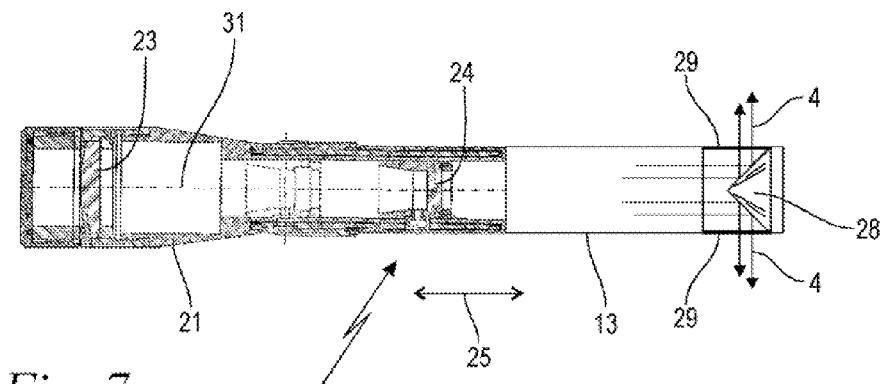
FIG. 7 shows a further variant of the handpiece according to FIG. 5 with a conical mirror for circular beam delivery.

FIG. 7 shows a further variant of the hand piece according to FIG. 6, wherein the flat mirror 26 (FIG. 6) is replaced by a conical mirror 28. The conical mirror 28 is held to the adapter piece body by struts 29 with openings in between, allowing the laser beam 4 to exit the adapter piece 13 in a radial direction. Because of the conical shape of the mirror 28, the laser beam 4 is spread in all radial directions thereby producing a cylindrical irradiation pattern around the longitudinal axis 31. The features according to the irradiation pattern of FIG. 2 apply analogously.

Unless otherwise explicitly stated, the embodiments of FIGS. 5, 6 and 7 are identical to each other with respect to the remaining features and reference numerals. The same applies to the embodiment of FIG. 1.

Figure 8:
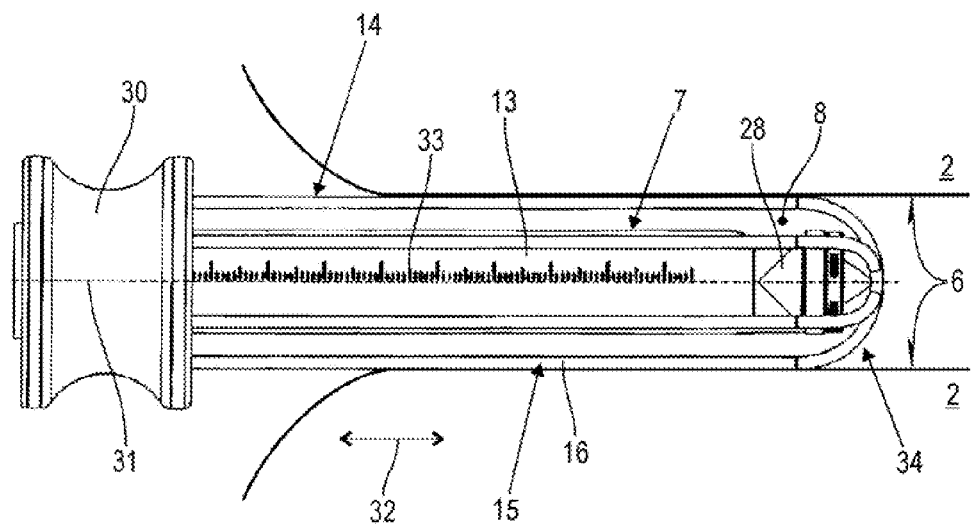
FIG. 8 is a side view of an inventive guide element with an inserted adapter piece of the handpiece according to FIG. 7.

FIG. 8 shows in a side view a further aspect of the invention, wherein the laser system 1 according to FIGS. 1 to 7 further comprises a guide element 14. For the sake of simplicity, only the adapter piece 13 of the hand piece 7 according to FIG. 7 is shown and coaxially inserted into the guide element 14.

The entire arrangement according to FIG. 8 is adapted for treatment of mucosa tissue within body openings and in particular within a woman's vagina, thereby acting as a vaginal inserter. In particular, said arrangement for non-ablative treatment of mucosa 2 on the inner vaginal walls is utilized to provide a laser assisted stress urinary incontinence treatment or a laser vaginal tightening treatment. The guide element 14 is inserted in the schematically sketched vagina with its mucosa tissue 2 walls circumferentially surrounding the guide element 14, thereby providing a target area 6 and an irradiation area 8 radially positioned relative to the guide element 14 and the handpiece 7.

The guide element 14 comprises radial distance means 15, which hold the circumferential target area 6 of the mucosa tissue 2 in a desired radial distance to the adapter piece 13 and its conical mirror 28 or, if an adapter piece 13 according to FIG. 6 is used, to its flat mirror 26. In the shown embodiment, the radial distance means 15 are comprised of a number of struts 16, being disposed axially parallel to the longitudinal axis 31 of the hand piece 7, and are fixed to a grip 30. At their opposite distal end the struts 16 have curved ends 34, by means of which they are connected to each other.

The guide element 14 serves as a receptacle and guide for the adapter piece 13 in that the hand piece 7 including its adapter piece 13 is longitudinally and slidingly movable coaxial to the longitudinal axis 31 relative to the guide element 14 as indicated by an arrow 32. The grip 30 therefore serves as a slide bearing. During operation the guide element 14 is inserted into the vagina and held there in place without any further movement. The hand piece 7 is inserted with its adapter piece 13 into the guide element 14 up to a desired insertion depth, for the control of which a depth scale 33 is engraved on the outer circumferential wall of the adapter piece 13.

Within one application session, by longitudinally moving the hand piece 7 including its adapter piece 13 relative to the fixed guide element 14, the laser beam 4 is guided over the target area 6 in at least one stepped pass such, that adjacent irradiation areas 8 of individual movement steps have an overlap preferably in a range from 10%, inclusive, to 70%, inclusive. Preferably multiple passes within one application session are chosen. In this case, between two sequential passes the guide element 14 may be turned about its longitudinal axis. This prevents the target area 6 of being shielded by the longitudinal struts 16 against the laser beam 4 during the present pass at the same location as during the previous pass. In the shown preferred embodiment, the guide element 14 comprises six struts 16 in a circumferential equal spacing of 60°. In this case, the guide element 14 should be turned at least approximately by 30° about its longitudinal axis. However, different angles and angle combinations may be desired as well. In order to expedite a correct turning movement of the guide element 14, it may comprise a marking or scale in particular on the outer end of its grip 30.

The conical mirror 28 of FIGS. 7, 8 provides a circumferential irradiation of a cylindrical irradiation area 8 on the target area 6 analogous to FIG. 2. In particular the target area 6 is defined by the 360° circumferential inner vaginal wall. Upon an axial movement of the hand piece 7 relative to the resting guide element 14 in the direction of the arrow 32 the irradiation area 8 is moved as well, thereby irradiating the entire target area 6 to any extend as desired. Preferably, within one application session the adapter piece 13 is longitudinally moved relative to the guide element 14 in at least one, preferably in two to six, and in particular in four passes, wherein the longitudinal movement is performed in fifteen to twenty-five, in particular in twenty steps.

Instead of the embodiment with the conical mirror 28, a hand piece 7 according to FIG. 6 with a flat mirror 26 may be used together with the guide element 14 of FIG. 8, thereby producing an irradiation area 8 according to FIG. 2 on the circumferential target area 6. Besides the a.m. axial movement of the hand piece 7, the hand piece 7 may additionally be rotated about its longitudinal axis 31 relative to the resting guide element 14, thereby moving the irradiation area 8 (FIG. 2) in the circumferential direction. With a combined axial and rotational movement, any desired shape and size of the target area 6 may be irradiated.

In a preferred specific application and process wherein the target area 6 is defined by the anterior vaginal wall rather than the a.m. 360° circumferential inner vaginal wall. In this case the adapter piece 13 having an angular flat mirror 26 is again at least longitudinally moved within the guide element 14, thereby guiding the laser beam 4 over the target area 6. Within one application session the adapter piece 13 is longitudinally moved relative to the guide element 14 expediently in at least one, preferably in three to seven, and in particular in five passes, wherein the longitudinal movement is performed in fifteen to twenty-five, in particular in nineteen steps. In the case of multiple passes, between each individual pass the adapter piece 13 with the angular flat mirror 35 is turned such, that the laser beam 4 is guided onto a sub-area of the target area 6 circumferentially adjacent to and overlapping with a sub-area already being irradiated during a preceding pass.

The axial and/or rotational movement of the hand piece 7 relative to the guide element 14 is performed by hand. However, a motor driven movement, which may be controlled by the control unit 5 (FIG. 1) may be chosen as well.

Figure 9:
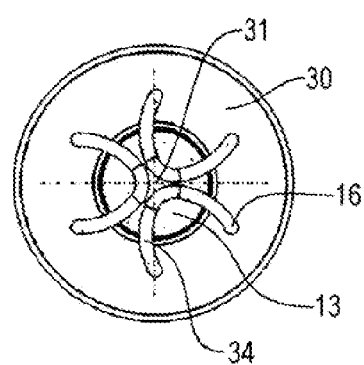
FIG. 9 is a top view of the arrangement according to FIG. 8 with details of circumferentially arranged struts as radial distance means.

FIG. 9 shows a top view of the arrangement according to FIG. 8, according to which a total of six struts 16 are evenly distributed around the adapter piece 13, its longitudinal axis 31 and the longitudinal axis of the guide element 14 respectively. It can be seen, that each two struts 16 are connected to each other with their curved ends 34 and being made of one single wire piece. Three such pairs are connected to each other close to the longitudinal axis 31, thereby forming a rigid structure.

The above described inventive laser system may be used for any kind of non ablative, thermal treatment of soft tissue like human mucosa. Some specific treatment scenarios are mentioned in the following:

For non invasive laser vaginal modification for sexual gratification enhancement by means of the above described inventive laser system 1 the delivered laser beam generates controlled heat on vaginal structures. A patient experiences an immediate change (tightening) of her vaginal walls, which in turn facilitates the production of higher friction during sexual intercourse, providing enhancement of sexual gratification. This procedure is performed in a short 10 minute treatment session and requires no anesthesia. No cuts or wounds are inflicted so all potential undesired collateral effects are minimized. The emission of controlled heat deposition of between 50-70° C. is achieved thanks to the high content of water in vaginal mucosa coupled with the high absorption that the erbium:YAG laser has in water. This not only provides immediate tightening of the tissue but also generates enough damage to the collagen in order to trigger a natural process of collagen renewal, which in turn enhances tightening even more and prolongs the benefits of the immediate result. Since the surrounding endopelvic fascia is composed of 85% collagen the collagenogenesis process is maximized providing long term sustainability of the treatment. Patient does not require pre-treatment of any kind. Laser treatment covers the complete internal vaginal walls, vestibule, hymenal caruncles and the fourchette. Two complete passes are performed over the described area, and a third reinforcement pass is done on the hymenal caruncles. No post-op treatment is necessary. Normal sexual activity is resumed after five days post-treatment.

With respect to laser treatment of urinary incontinence (UI) the inventive laser system allows the doctor to make thermal tension and shrinking of endopelvic fascia and pelvic floor, applying the laser to the region of urethral and anterior bladder wall. The intense and deep thermal stimulus will produce the collagenogenesis which consolidates the long-term outcome. These effects are applicable in stress urinary incontinence, vaginal rejuvenation, cystocele and rectocele. The treatment procedure involves laser irradiation of the mucosa at the urogenital diaphragm.

The urogenital treatment is performed in such a way that patterned laser beam is applied firstly across the vestibule and around the urethral orifice and after that along the anterior vaginal wall. Two to three passes across the whole area have to be applied in the first session of laser therapy. Depending on the severity of incontinence in ca. 25% of cases the second treatment could be necessary after the period of one month to 6 weeks.

For a laser assisted snoring reduction the inventive laser system involves non ablative Er:YAG tightening of uvula, soft palate and surrounding tissues. The laser beam is fired at soft intraoral tissue with repetition rate, and delivered, either vertically or horizontally (depending on the region). Seven to eight passes are performed across each region (with 50% overlap). The treated tissue is thermally processed and consequently it shrinks. Treatment sessions are performed at day 1, 15 and 45.

The specification incorporates by reference the entire disclosure of European priority application EP 11 000 182.3 having a filing date of 12 Jan. 2011.

While specific, embodiments of the invention have been shown and described in detail to illustrate the inventive principles, it will be understood that the invention may be embodied otherwise without departing from such principles.

What is claimed is:

1. A method for non-ablative treatment of mucosa tissue by using a laser system comprising a laser source for generating a laser beam, a control unit and a hand piece, wherein the laser beam is manually guided onto a target area on the mucosa tissue, wherein a wavelength ($\lambda$) of the laser beam is in a range from above 1.9 µm to 11.0 µm inclusive, the method comprising:

Generating with the laser source under control of the control unit the laser beam in at least one pulse sequence, wherein said at least one pulse sequence consists of a number of single pulses with a pulse duration ($t_p$) in a range from 1.0 µs, inclusive, to 1.0 sec, inclusive, wherein the number of single pulses is in a single pulse range of two to fifteen;

wherein the single pulses each provide on the target area of the mucosa tissue a fluence in a fluence range from 0.2 J/cm$^2$, inclusive;

wherein a sequence duration ($t_s$) of said at least one pulse sequence is in a range from 50.0 ms, inclusive, to 1,000.0 ms, inclusive;

Adjusting, in said at least one pulse sequence, the fluence within said fluence range and the number of said single pulses within said single pulse range and applying said at least one pulse sequence to the mucosa tissue such that heat is deposited into the mucosa tissue in a controlled manner to a depth of at least 100 µm and that the mucosa tissue is heated within said depth to a range from 50 degrees Celsius to 70 degrees Celsius.

2. The method according to claim 1, providing as the laser source an Er:YAG laser with a wave length (l) of 2.94 µm or an Er,Cr:YSGG laser with a wave length (l) in the range from 2.73 µm, inclusive, to 2.79 µm, inclusive, or a CO$_2$ laser with a wave length ($\lambda$) of 10.6 µm.

3. The method according to claim 1, utilizing the non-ablative treatment of mucosa to provide a laser assisted snoring reduction.

4. The method according to claim 1, utilizing the non-ablative treatment of mucosa to provide a laser assisted stress urinary incontinence treatment or a laser vaginal tightening treatment.

5. The method according to claim 1, irradiating, with the hand piece resting, an irradiation area on the target area such that the irradiation area has a mean area diameter in a range from 0.3 mm, inclusive, to 20.0 mm, inclusive.

6. The method according to claim 1, irradiating, with the hand piece resting, an irradiation area on the target area in single target dots having a mean dot diameter in a range from 0.3 mm, inclusive, to 3.0 mm, inclusive.

7. The method according to claim 6, generating the single target dots by a scanner, a screen, a lens array or a diffractional lens.

8. The method according to claim 1, irradiating, with the hand piece resting, an irradiation area on the target area and guiding within one application session the laser beam over the target area in at least one pass such that adjacent irradiation areas have an overlap in a range from 10%, inclusive, to 70%, inclusive.

9. The method according to claim 1, guiding the laser beam, for providing a non-ablative treatment of mucosa tissue, onto mucosa tissue and applying the pulse sequence comprising four to eight single pulses, wherein the sequence duration ($t_s$) is in a range from 100.0 ms, inclusive, to 500.0 ms, inclusive.

10. The method according to claim 9, wherein the cumulative fluence of the single pulses of a single pulse sequence on a target area of the mucosa tissue is in a range from 2.0 J/cm$^2$, inclusive, to 20.0 J/cm$^2$, inclusive.

11. The method according to claim 9, wherein several of the pulse sequences follow each other with a sequence repetition time ($t_{sr}$) in a range from 0.5 s, inclusive, to 2.0 s, inclusive.

12. The method according to claim 11, wherein two to six of the pulse sequences are sequentially guided across the same location within the target area.

13. The method according to claim 9, wherein when the mucosa on the inner vaginal walls is treated to provide a laser assisted stress urinary incontinence treatment or a laser vaginal tightening treatment, the hand piece has an exit side, wherein an adapter piece is disposed on the exit side and a guide element as a receptacle and guide for the adapter piece is provided, the method comprising:

inserting the guide element into the inner vagina and bringing the guide element in immediate contact with the target area;

moving the adapter piece longitudinally and/or rotationally within the guide element to guide the laser beam over the target area in multiple passes within at least one application session.

14. The method according to claim 13, wherein the guide element comprises longitudinal struts, the method comprising:

guiding the laser beam within at least one application session over the target area in multiple passes;

turning between two sequential passes the guide element about its longitudinal axis so as to prevent the target area from being shielded against the laser beam by the longitudinal struts at the same location.

15. The method according to claim 13, comprising the steps of using an adapter piece having an angular flat mirror to provide a laser assisted stress urinary incontinence treatment or a laser vaginal tightening treatment, wherein the target area is defined by the anterior vaginal wall, and moving the adapter piece at least longitudinally within the guide element to guide the laser beam over the target area.

16. The method according to claim 15, wherein within one application session the adapter piece is longitudinally moved relative to the guide element in one or several passes, wherein the longitudinal movement is performed in fifteen to twenty-five steps, and wherein, when several passes are carried out, between sequential passes the adapter piece with the angular flat mirror is turned such, that the laser beam is guided onto a sub-area of the target area adjacent to and overlapping with a sub-area already being irradiated during a preceding pass.

17. The method according to claim 13, comprising the steps of using an adapter piece having a conical mirror to provide a laser assisted stress urinary incontinence treatment or a laser vaginal tightening treatment, wherein the target area is defined by the 360° circumferential vaginal wall, and moving the adapter piece at least longitudinally moved within the guide element to guide the laser beam over the target area.

18. The method according to claim 17, wherein within one application session the adapter piece is longitudinally moved relative to the guide element in at least one pass, wherein the longitudinal movement is performed in fifteen to twenty-five steps.

\* \* \* \* \*